US008173123B2

(12) United States Patent
Strober et al.

(10) Patent No.: US 8,173,123 B2
(45) Date of Patent: May 8, 2012

(54) METHODS OF TREATING COLITIS INVOLVING IL-13 AND NK-T CELLS

(75) Inventors: Warren Strober, Bethesda, MD (US); Ivan J. Fuss, Bethesda, MD (US); Frank Heller, Berlin (DE); Richard Blumberg, Chestnut Hill, MA (US)

(73) Assignees: The United States of America, as represented by the Secretary, Department of Health and Human Services, Washington, DC (US); Brigham & Women's Hospital, Boston, MA (US)

( * ) Notice: Subject to any disclaimer, the term of this patent is extended or adjusted under 35 U.S.C. 154(b) by 0 days.

(21) Appl. No.: 12/709,029

(22) Filed: Feb. 19, 2010

(65) Prior Publication Data
US 2010/0143339 A1 Jun. 10, 2010

Related U.S. Application Data

(62) Division of application No. 10/517,898, filed as application No. PCT/US02/18790 on Jun. 14, 2002, now Pat. No. 7,666,411.

(51) Int. Cl.
*A61K 39/395* (2006.01)
(52) U.S. Cl. .................................................. 424/130.1
(58) Field of Classification Search .................. None
See application file for complete search history.

(56) References Cited

U.S. PATENT DOCUMENTS

| | | | |
|---|---|---|---|
| 5,614,191 A | 3/1997 | Puri et al. | |
| 5,830,453 A | 11/1998 | Badr et al. | |
| 5,965,401 A | 10/1999 | Chang et al. | |
| 6,030,613 A | 2/2000 | Blumberg et al. | |
| 6,140,076 A | 10/2000 | Adema et al. | |
| 6,143,871 A | 11/2000 | Bonnefoy et al. | |
| 6,274,338 B1 | 8/2001 | Glimcher | |
| 6,358,508 B1 | 3/2002 | Ni et al. | |
| 6,518,061 B1 | 2/2003 | Puri et al. | |
| 7,666,411 B2* | 2/2010 | Strober et al. ............. | 424/130.1 |
| 2002/0042387 A1 | 4/2002 | Raz et al. | |
| 2004/0022787 A1 | 2/2004 | Cohen et al. ............. | 424/144.1 |
| 2004/0023337 A1 | 2/2004 | Heavner et al. ............ | 435/69.52 |
| 2004/0043921 A1 | 3/2004 | Bonnefoy et al. | |
| 2006/0002927 A1* | 1/2006 | Exley et al. ................ | 424/144.1 |
| 2009/0092543 A1* | 4/2009 | Strober et al. ............. | 424/1.41 |

FOREIGN PATENT DOCUMENTS

| | | |
|---|---|---|
| AU | 2002315115 | 1/2009 |
| WO | WO 00/02583 | 1/2000 |
| WO | WO 00/02923 | 1/2000 |
| WO | 00/64944 A1 | 11/2000 |
| WO | WO 00/64944 | 11/2000 |
| WO | 01/82960 A1 | 11/2001 |
| WO | WO 01/82960 | 11/2001 |
| WO | WO 03/080675 | 10/2003 |
| ZA | 2005/0375 | 8/2006 |

OTHER PUBLICATIONS

Huang Z., Pharmacology and Therapeutics, 2000, 86: 201-215.*
Balk, S. P., Bleicher, P. A., and Terhorst, C. (1989). Isolation and characterization of a cDNA and gene coding for a fourth CD1 molecule. Proc Natl Acad Sci U S A 86, 252-256.
Bendelac, A. (1995). Positive selection of mouse NK1+ T cells by CD1-expressing cortical thymocytes. J Exp Med 182, 2091-2096.
Bleicher, P. A., Balk, S. P., Hagen, S. J., Blumberg, R. S., Flotte, T. J., and Terhorst, C. (1990). Expression of murine CD1 on gastrointestinal epithelium. Science 250, 679-682.
Blumberg, R. S., Terhorst, C., Bleicher, P., McDermott, F. V., Allan, C. H., Landau, S. B., Trier, J. S., and Balk, S. P. (1991). Expression of a nonpolymorphic MHC class I-like molecule, CD1D, by human intestinal epithelial cells. J Immunol 147, 2518-2524.
Boirivant, M., Fuss, I. J., Chu, A., and Strober, W. (1998). Oxazolone colitis: A murine model of T helper cell type 2 colitis treatable with antibodies to interleukin 4. J Exp Med 188, 1929-1939.
Bonish B, Jullien D, Dutronc Y, Huang BB, Modlin R, Spada FM, Porcelli SA, Nickoloff BJ. Overexpression of CD1d by keratinocytes in psoriasis and CD1d-dependent IFN-gamma production by NK-T cells. J Immunol. Oct. 1, 2000;165(7):4076-85.
Brown, KD, Zurawski SM, Mosmann TR, Zurawski G. A family of small inducible proteins secreted by leukocytes are members of a new superfamily that includes leukocyte and fibroblast-derived inflammatory agents, growth factors, and indicators of various activation processes *J. Immunol.* 142 (2), 679-687 (1989).
Brown, M. A., and Hural, J. (1997). Functions of IL-4 and control of its expression. Crit Rev Immunol 17, 1-32.
Brown, TE, Bankhurst AD, Strickland RG, Natural killer cell function and lymphocyte subpopulation profiles in inflammatory bowel disease. J Clin Lab Immunol. Jul. 1983;11(3)113-7.
Camoglio L, Te Velde AA, Tigges AJ, Das PK, Van Deventer SJ. Altered expression of interferon-gamma and interleukin-4 in inflammatory bowel disease. Inflamm Bowel Dis. Nov. 1998;4(4):285-90.
Ceponis, P. J., Botelho, F., Richards, C. D., and McKay, D. M. (2000). Interleukins 4 and 13 increase intestinal epithelial permeability by a phosphatidylinositol 3-kinase pathway. Lack of evidence for STAT 6 involvement. J Biol Chem 275, 29132-29137.
Chen, H., and Paul, W. E. (1997). Cultured NK1.1+ CD4+ T cells produce large amounts of IL-4 and IFN- gamma upon activation by anti-CD3 or CD1. J Immunol 159, 2240-2249.

(Continued)

*Primary Examiner* — Ilia Ouspenski
(74) *Attorney, Agent, or Firm* — Edwards Wildman Palmer LLP; Peter F. Corless; Andrew W. Shyjan, Esq.

(57) ABSTRACT

Method of treating or preventing the inflammatory response of colitis in a subject comprising administering to the subject an effective amount of a substance that modulates IL-13 activity (FIG. 3). The invention also provides a method of treating or preventing the inflammatory response of colitis in a subject comprising administering to the subject an effective amount of a substance that modulates NK-T cell activity. The invention also provides for the screening of substances that treat or prevent the inflammatory response of colitis.

4 Claims, 6 Drawing Sheets

OTHER PUBLICATIONS

Cui, J., Shin, T., Kawano, T., Sato, H., Kondo, E., Toura, I., Kaneko, Y., Koseki, H., Kanno, M., and Taniguchi, M. (1997). Requirement for Valpha14 NKT cells in IL-12-mediated rejection of tumors. Science 278, 1623-1626.

del Mar Cabrera M, Valle J, Pajares JM, Romero I, Zomeno M, Mate J. Expression of the Kp43 (CD 94) receptor by natural killer (NK) cells in ulcerative colitis. Hepatogastroenterology. Sep.-Oct. 2001;48(41):1316-20.

Desreumaux P, Brandt E, Gambiez L, Emilie D, Geboes K, Klein O, Ectors N, Cortot A, Capron M, Colombel JF. Distinct cytokine patterns in early and chronic ileal lesions of Crohn's disease. Gastroenterology Jul. 1997;113(1):118-26.

Dolganov, et al. "Coexpression of the interleukin-13 and interleukin-4 genes correlates with their physical linkage in the cytokine gene cluster on human chromosome 5q23-31" Blood 87 (8), 3316-3326 (1996).

Donaldson, D. D., Whitters, M. J., Fitz, L. J., Neben, T. Y., Finnerty, H., Henderson, S. L., O'Hara, R. M., Jr., Beier, D. R., Turner, K. J., Wood, C. R., and Collins, M. (1998). The murine IL-13 receptor alpha 2: molecular cloning, characterization, and comparison with murine IL-13 receptor alpha 1. J Immunol 161, 2317-2324.

Fiocchi C, Tubbs RR, Youngman KR. Human intestinal mucosal mononuclear cells exhibit lymphokine-activated killer cell activity. Gastroenterology. Mar. 1985;88(3):625-37.

Fiorentino, D. F., Zlotnik, A., Vieira, P., Mosmann, T. R., Howard, M., Moore, K. W., and O'Garra, A. (1991). IL-10 acts on the antigen-presenting cell to inhibit cytokine production by Th1 cells. J Immunol 146, 3444-3451.

Fort, M. M., Cheung, J., Yen, D., Li, J., Zurawski, S. M., Lo, S., Menon, S., Clifford, T., Hunte, B., Lesley, R., et al. (2001). IL-25 induces IL-4, IL-5, and IL-13 and Th2-associated pathologies in vivo. Immunity 15, 985-995.

Fuss, I. J., Neurath, M., Boirivant, M., Klein, J. S., de la Motte, C., Strong, S. A., Fiocchi, C., and Strober, W. (1996). Disparate CD4+ lamina propria (LP) lymphokine secretion profiles in inflammatory bowel disease. Crohn's disease LP cells manifest increased secretion of IFN-gamma, whereas ulcerative colitis LP cells manifest increased secretion of IL-5. J Immunol 157, 1261-1270.

Ginsburg CH, Dambrauskas JT, Ault KA, Falchuk ZM. Impaired natural killer cell activity in patients with inflammatory bowel disease: evidence for a qualitative defect. Gastroenterology. Oct. 1983;85(4):846-51.

Gumperz, J. E., Roy, C., Makowska, A., Lum, D., Sugita, M., Podrebarac, T., Koezuka, Y., Porcelli, S. A., Cardell, S., Brenner, M. B., and Behar, S. M. (2000). Murine CD1d-restricted T cell recognition of cellular lipids. Immunity 12, 211-221.

Hayakawa, K., Lin, B. T., and Hardy, R. R. (1992). Murine thymic CD4+ T cell subsets: a subset (Thy0) that secretes diverse cytokines and overexpresses the V beta 8 T cell receptor gene family. J Exp Med 176, 269-274.

Inoue S, Matsumoto T, Iida M, Mizuno M, Kuroki F, Hoshika K, Shimizu M. Characterization of cytokine expression in the rectal mucosa of ulcerative colitis: correlation with disease activity. Am J Gastroenterol. Sep. 1999;94(9):2441-6.

Ishikawa, H., Hisaeda, H., Taniguchi, M., Nakayama, T., Sakai, T., Maekawa, Y., Nakano, Y., Zhang, M., Zhang, T., Nishitani, M., et al. (2000). CD4(+) v(alpha)14 NKT cells play a crucial role in an early stage of protective immunity against infection with Leishmania major. Int Immunol 12, 1267-1274.

Kadivar K, Defelice ML, Markowitz JE, Baldassano RN, Brown KA. Intestinal interleukin-13 in pediatric inflammatory bowel disease patients. [abstract]. J. Pediatr Gastroenterol Nutr. 2001 33(3):372.

Kaneko, Y., Harada, M., Kawano, T., Yamashita, M., Shibata, Y., Gejyo, F., Nakayama, T., and Taniguchi, M. (2000). Augmentation of Valpha14 NKT cell-mediated cytotoxicity by interleukin 4 in an autocrine mechanism resulting in the development of concanavalin A-induced hepatitis. J Exp Med 191, 105-114.

Kawano, T., Cui, J., Koezuka, Y., Toura, I., Kaneko, Y., Motoki, K., Ueno, H., Nakagawa, R., Sato, H., Kondo, E., et al. (1997). CD1d-restricted and TCR-mediated activation of valpha14 NKT cells by glycosylceramides. Science 278, 1626-1629.

Koyasu, S. (1994). CD3+CD16+NK1.1+B220+ large granular lymphocytes arise from both alpha-beta TCR+CD4-CD8- and gamma-delta TCR+CD4-CD8- cells. J Exp Med 179, 1957-1972.

Kucharzik T, Lugering N, Adolf M, Domschke W, Stoll R. Synergistic effect of immunoregulatory cytokines on peripheral blood monocytes from patients with inflammatory bowel disease. Dig Dis Sci. Apr. 1997;42(4):805-12.

Kumar, H., Belperron, A., Barthold, S. W., and Bockenstedt, L. K. (2000). Cutting edge: CD1d deficiency impairs murine host defense against the spirochete, Borrelia burgdorferi. J Immunol 165, 4797-4801.

Lakatos L. Immunology of inflammatory bowel diseases. Acta Physiol Hung. 2000;87(4):355-72.

Lantz, O., and Bendelac, A. (1994). An invariant T cell receptor alpha chain is used by a unique subset of major histocompatibility complex class I-specific CD4+ and CD4-8- T cells in mice and humans. J Exp Med 180, 1097-1106.

Lee, P. T., Benlagha, K., Teyton, L., and Bendelac, A. (2002). Distinct functional lineages of human V(alpha)24 natural killer T cells. J Exp Med 195, 637-641.

Lugering N, Kucharzik T, Stein H, Winde G, Lugering A, Hasilik A, Domschke W, Stoll R. IL-10 synergizes with IL-4 and IL-13 in inhibiting lysosomal enzyme secretion by human monocytes and lamina propria mononuclear cells from patients with inflammatory bowel disease. Dig Dis Sci. Apr. 1998;43(4):706-14.

Mack DR, Beedle S, Warren J, Davis J, Gross T. Peripheral blood intracellular cytokine analysis in children newly diagnosed with inflammatory bowel disease. Pediatr Res. Mar. 2002;51(3):328-32.

Manzano L, Alvarez-Mon M, Abreu L, Antonio Vargas J, de la Morena E, Corugedo F, Durantez A. Functional impairment of natural killer cells in active ulcerative colitis: reversion of the defective natural killer activity by interleukin 2. Gut. Feb. 1992;33(2):246-51.

Minty, A., Asselin, S., Bensussan, A., Shire, D., Vita, N., Vyakarnam, A., Wijdenes, J., Ferrara, P., and Caput, D. (1997). The related cytokines interleukin-13 and interleukin-4 are distinguished by differential production and differential effects on T lymphocytes. Eur Cytokine Netw 8, 203-213.

Miyamoto, K., Miyake, S., and Yamamura, T. (2001). A synthetic glycolipid prevents autoimmune encephalomyelitis by inducing TH2 bias of natural killer T cells. Nature 413, 531-534.

Mizoguchi, A., Mizoguchi, E., and Bhan, A. K. (1999). The critical role of interleukin 4 but not interferon gamma in the pathogenesis of colitis in T-cell receptor alpha mutant mice. Gastroenterology 116, 320-326.

Moore, K. W., O'Garra, A., de Waal Malefyt, R., Vieira, P., and Mosmann, T. R. (1993). Interleukin-10. Annu Rev Immunol 11, 165-190.

Neurath, M. F., Fuss, I., Kelsall, B. L., Stuber, E., and Strober, W. (1995). Antibodies to interleukin 12 abrogate established experimental colitis in mice. J Exp Med 182, 1281-1290.

Park, S. H., Roark, J. H., and Bendelac, A. (1998). Tissue-specific recognition of mouse CD1 molecules. J Immunol 160, 3128-3134.

Parronchi, P., Romagnani, P., Annunziato, F., Sampognaro, S., Becchio, A., Giannarini, L., Maggi, E., Pupilli, C., Tonelli, F., and Romagnani, S. (1997). Type 1 T-helper cell predominance and interleukin-12 expression in the gut of patients with Crohn's disease. Am J Pathol 150, 823-832.

Radford-Smith G, Jewell DP. Cytokines and inflammatory bowel disease. Baillieres Clin Gastroenterol. Mar. 1996;10(1):151-64.

Roark, J. H., Park, S. H., Jayawardena, J., Kavita, U., Shannon, M., and Bendelac, A. (1998). CD1.1 expression by mouse antigen-presenting cells and marginal zone B cells. J Immunol 160, 3121-3127.

Rogler G, Andus T. Cytokines in inflammatory bowel disease. World J Surg. Apr. 1998;22(4):382-9.

Sartor, R. B. (1995). Current concepts of the etiology and pathogenesis of ulcerative colitis and Crohn's disease. Gastroenterol Clin North Am 24, 475-507.

Saubermann LJ, Beck P, De Jong YP, Pitman RS, Ryan MS, Kim HS, Exley M, Snapper S, Balk SP, Hagen SJ, Kanauchi O, Motoki K, Sakai T, Terhorst C, Koezuka Y, Podolsky DK, Blumberg RS. Activation of natural killer T cells by alpha-galactosylceramide in the presence of CD1d provides protection against colitis in mice. Gastroenterology. Jul. 2000;119(1):119-28.

Scheiffele, F., Fuss, I. (2002). Induction of TNBS colitis in mice, vol. 15.19, John Wiley & Sons, Inc.).
Shinoda M, Haruta J, Tanimoto M, Ando T, Hosokawa T, Ina K, Kusugami K. Lamina propria mononuclear cells express and respond to interleukin-2 differently in Crohn's disease and ulcerative colitis. Intern Med. Sep. 1996;35(9):679-85.
Singh B, Powrie F, Mortensen NJ. Immune therapy in inflammatory bowel disease and models of colitis. Br J Surg. Dec. 2001;88(12):1558-69.
Smiley, S. T., Kaplan, M. H., and Grusby, M. J. (1997). Immunoglobulin E production in the absence of interleukin-4-secreting CD1-dependent cells. Science 275, 977-979.
Sonoda, K. H., Exley, M., Snapper, S., Balk, S. P., and Stein-Streilein, J. (1999). CD1-reactive natural killer T cells are required for development of systemic tolerance through an immune-privileged site. J Exp Med 190, 1215-1226.
Spada, F. M., Koezuka, Y., and Porcelli, S. A. (1998). CD1d-restricted recognition of synthetic glycolipid antigens by human natural killer T cells. J Exp Med 188, 1529-1534.
Strober W, Fuss IJ, Blumberg RS. The immunology of mucosal models of inflammation. Annu Rev Immunol. 2002;20:495-549. Epub Oct. 4, 2001.
Strober, S., Cheng, L., Zeng, D., Palathumpat, R., Dejbakhsh-Jones, S., Huie, P., and Sibley, R. (1996). Double negative (CD4-CD8- alpha beta+) T cells which promote tolerance induction and regulate autoimmunity. Immunol Rev 149, 217-230.
Takeda, K., Hayakawa, Y., Van Kaer, L., Matsuda, H., Yagita, H., and Okumura, K. (2000). Critical contribution of liver natural killer T cells to a murine model of hepatitis. Proc Natl Acad Sci U S A 97, 5498-5503.
Tamura J, Jinbo T, Itoh K, Take H, Matsushima T, Murakami H, Kubota K, Tsuchiya J, Naruse T. Suppressed natural killer cell activity in ulcerative colitis. J Med. 1994;25(5):337-40.
Terabe, M., Matsui, S., Noben-Trauth, N., Chen, H., Watson, C., Donaldson, D. D., Carbone, D. P., Paul, W. E., and Berzofsky, J. A. (2000). NKT cell-mediated repression of tumor immunosurveillance by IL-13 and the IL-4R-STAT6 pathway. Nat Immunol 1, 515-520.
Urban, J. F., Jr., Noben-Trauth, N., Donaldson, D. D., Madden, K. B., Morris, S. C., Collins, M., and Finkelman, F. D. (1998). IL-13, IL-4Ralpha, and Stat6 are required for the expulsion of the gastrointestinal nematode parasite *Nippostrongylus brasiliensis*. Immunity 8, 255-264.
Vainer B, Nielsen OH, Hendel J, Horn T, Kirman I. Colonic expression and synthesis of interleukin 13 and interleukin 15 in inflammatory bowel disease. Cytokine. Oct. 2000;12(10):1531-6.
van Tol EA, Verspaget HW, Pena AS, Lamers CB. Normal inflammatory bowel disease mucosa conceals alterations in natural killer cell activity. Scand J Gastroenterol. Dec. 1992;27(12):999-1005.
Vezys, V., Olson, S., and Lefrancois, L. (2000). Expression of intestine-specific antigen reveals novel pathways of CD8 T cell tolerance induction. Immunity 12, 505-514.
Wills-Karp, M., Luyimbazi, J., Xu, X., Schofield, B., Neben, T. Y., Karp, C. L., and Donaldson, D. D. (1998). Interleukin-13: central mediator of allergic asthma. Science 282, 2258-2261.
Yoshimoto, T., and Paul, W. E. (1994). CD4pos, NK1.1pos T cells promptly produce interleukin 4 in response to in vivo challenge with anti-CD3. J Exp Med 179, 1285-1295.
Zurawski, G., and de Vries, J. E. (1994). Interleukin 13, an interleukin 4-like cytokine that acts on monocytes and B cells, but not on T cells. Immunol Today 15, 19-26.
Bost et al. "In vivo treatment with anti-interleukin-13 antibodies significantly reduces the humoral immune response against an oral immunogen in mice" *Immunol.* 87:633-64 (1996).
Chiaramonte et al. "IL-13 is a key regulator cytokine for Th2 cell-mediated pulmonary granuloma rormation and IgE responses induced by *S. mansoni* eggs" *J. Immunol.* 162(2):920-930 (1999).
Grünig et al. "Requirement for IL-13 independently of IL-4 in experimental asthma" *Science* 282:2261-2263 (Dec. 18, 1998).
Hans et al. "Interleukin 12 induced interferon-γ increases inflammation in acute dextran sulfate sodium induced colitis in mice" *Eur. Cytokine Netw* 11:67-74 (Mar. 2000).
Shalaby et al. "In vivo augmentation of natural killer activity by combined treatment with recombinant gamma interferon and Interleukin-2" *J Interferon Research* 5:571-581 (1985).
Verdú et al. "Modulatory effects of estrogen in two murine models of experimental colitis" *Am J Physiol Gastrointest Liver Physiol* 283:G27-G36 (2002).
Kawada et al., World J. Gastroenterol., 2007, 14: 5581-5593.
Heller et al., Immunity, 2002, 17: 629-638.
L.J. Saubermann et al., "Activation of Natural Killer T Cells by alpha-Galactosylceramide in the Presence of CD1d Provides protection against Colitis in Mice", Gastroenterology, 119(1), pp. 119-128 (2000).
M. Boirivant et al., "Oxazolone Colitis: A Murine Model of T Helper Cell Type 2 Colitis Treatable with Antibodies to Interleukin 4", The Journal of Experimental Medicine, 188(10), pp. 1929-1939 (1998).
M.F. Neurath et al., "Antibodies to Interleukin 12 Abrogate Established Experimental Colitis in Mice", The Journal of Experimental Medicine, vol. 182, pp. 1281-1290 (1995).
K.L. Bost et al., "In vivo treatment with anti-interleukin-13 antibodies significantly reduces the humoral immune response against an oral immunogen in mice", Immunology, vol. 87, pp. 633-641 (1996).
M.G. Chiaramonte et al., "IL-13 is a Key Regulatory Cytokine for Th2 Cell-Mediated Pulmonary Granulome Formation and IgE Responses Induced by *Schistosoma mansoni* Eggs", Journal of Immunology, 162(2), pp. 920-930 (1999).
E.F. Verdu et al., "Modulatory effects of estrogen in two murine models of experimental colitis", American Journal of Physiology-Gastrointestinal and Liver Physiology, 283(1), pp. G27-G36 (2002).
G. Gruenig et al., "Requirement for IL-13 Independently of IL-4 in Experimental Asthma", Science, vol. 282, pp. 2261-2263 (1998).
W.J. Sandborn et al., "Biologic Therapy of Inflammatory Bowel Disease", Gastroenterology, 122(6), pp. 1592-1608 (2002).
S. Okamoto et al., "A synthetic mimetic of CD4 is able to suppress disease in a rodent model of immune colitis", Eur. J. Immunol., vol. 29, pp. 355-366 (1999).

* cited by examiner

METHODS OF TREATING COLITIS INVOLVING IL-13 AND NK-T CELLS

CROSS REFERENCE TO RELATED APPLICATIONS

This application is a divisional application of U.S. application Ser. No. 10/517,898, filed on Jul. 27, 2005, now issued as U.S. Pat. No. 7,666,411, which is a National Phase Application based on PCT/US2002/018790, filed on Jun. 14, 2002. Both applications are incorporated by reference in their entirety.

BACKGROUND OF THE INVENTION

1. Field of the Invention

The present invention relates to a method of treating or preventing colitis by modulating the colitis-inducing effects of the cytokine interleukin-13 (IL-13). The invention also relates to a method of treating or preventing colitis by modulating the colitis-inducing effects of NK-T cells Further provided is a method for screening substances for their effectiveness in reducing the inflammatory response of colitis and preventing colitis in a mouse model.

2. Background Art

Human inflammatory bowel diseases (IBDs), Crohn's disease (CD), and ulcerative colitis (UC), are believed to be due to an abnormal mucosal T cell responsiveness to bacterial antigens in the gut lumen (Sartor, 1995). In CD, the responding T cells exhibit a Th1 phenotype and thus produce large amounts of interferon-γ (IFN-γ) and tumor necrosis factor (TNF-α). IL-12 secretion, the driving force of Th1 differentiation is also increased (Parronchi et al., 1997). In UC, the responding T cell is less well defined. In this case, whereas Th1 cytokine production is normal or decreased and some Th2 cytokine production (IL-5 and IL-10) is increased, the production of the "signature" cytokine of the Th2 response, IL-4, is not increased (Fuss et al., 1996).

SUMMARY OF THE INVENTION

The present invention provides a method of treating or preventing the inflammatory response of colitis in a subject comprising administering to the subject an effective amount of a substance that modulates NK-T cell activity.

Also provided by the present invention is a method of treating or preventing the inflammatory response of colitis in a subject comprising administering to the subject an effective amount of a substance that modulates IL-13 activity.

Also provided by the present invention is a method of screening a substance for effectiveness in reducing the inflammatory response of colitis by modulating IL-13 activity comprising: a) obtaining an animal having colitis; b) administering the substance to an animal; and assaying the animal for an effect on IL-13 activity which results in the reduction of the inflammatory response of the colitis, thereby identifying a substance effective in reducing the inflammatory response of colitis by modulating IL-13 activity.

Further provided by the present invention is a method of screening a substance for effectiveness in reducing the inflammatory response of colitis by modulating NK-T cell activity comprising: a) obtaining an animal having colitis; b) administering the substance to an animal; and c) assaying the animal for an effect on NK-T cell activity which results in the reduction of the inflammatory response of the colitis, thereby identifying a substance effective in reducing the inflammatory response of colitis by modulating NK-T cell activity.

The present invention also provides a method of screening for a substance effective in preventing the inflammatory response of colitis by modulating IL-13 activity comprising: a) administering the substance to an animal susceptible to colitis :b) subjecting the animal to treatment that will induce an inflammatory response; and c) assaying inflammatory tissue cells from the animal for an amount of secretion of IL-13, whereby a decrease or lack of increase in the amount of IL-13 in the inflammatory tissue cells of the animal as compared to an increase in the amount of IL-13 in a control animal having colitis in the absence of the substance identifies a substance that is effective in preventing the inflammatory response of colitis by modulating IL-13 activity.

Also provided by the present invention is a method of screening for a substance effective in preventing the inflammatory response of colitis by modulating NK-T cell activity comprising: a) administering the substance to an animal susceptible to colitis; b) subjecting the animal to treatment that will induce an inflammatory response; and c) assaying the animal for an effect on NK-T cell activity, whereby a decrease or lack of increase in NK-T cell activity in the inflammatory tissue cells of the animal as compared to an increase in NK-T cell activity in a control animal having colitis in the absence of the substance identifies a substance that is effective in preventing the inflammatory response of colitis by modulating NK-T cell activity.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
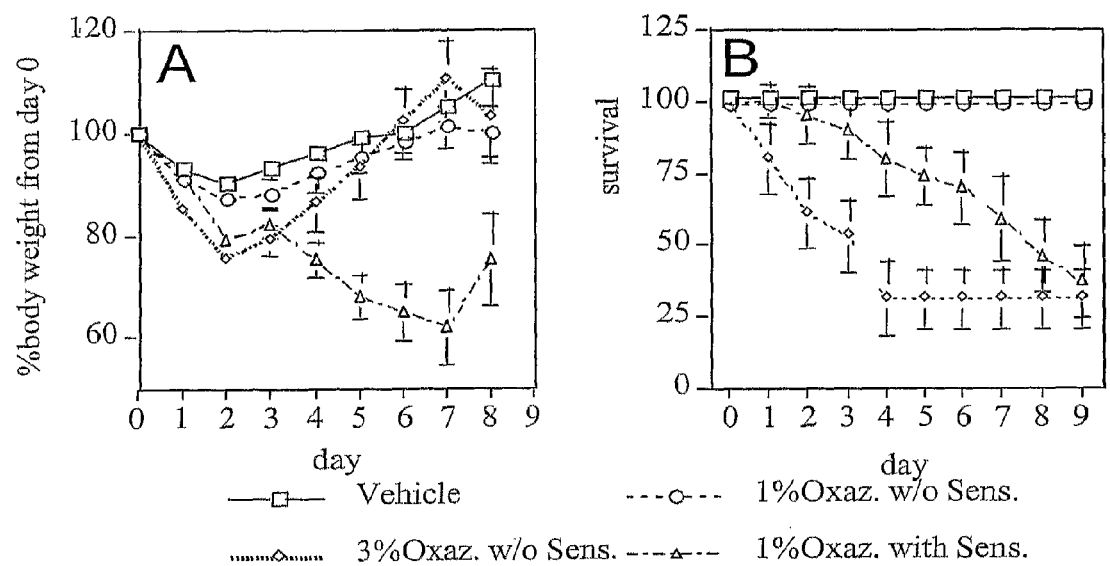
FIGS. 1A-F show that pre-sensitization before intra-rectal challenge with oxazalone leads to a chronic progressive colitis. Weight loss (A) and mortality (B) of mice after pre-sensitization with vehicle (ethanol) or oxazolone and intra-rectal challenge with vehicle or different doses of oxazolone 5× (C) and 10× (E) magnification of H.E. stained cross-sections from colons of mice 7 days after ethanol pre-sensitization and challenge. D+F show effects after oxazolone pre-sensitization and re-challenge with 1% oxazolone intra-rectally.

The present invention may be understood more readily by reference to the following detailed description of preferred embodiments of the invention and the Examples included therein and to the Figures and their previous and following description.

Before the present methods and compositions are disclosed and described, it is to be understood that this invention is not limited to specific methods or specific substances unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substance" includes one or more substances, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Methods of Treatment and Prevention

The present invention provides a method of treating or preventing the inflammatory response of colitis in a subject comprising administering to the subject an effective amount of a substance that modulates IL-13 activity.

Any animal which is subject to colitis (e.g., ulcerative colitis) can be treated by this method. Therefore, the subject can be any mammal, preferably human, and can include but is not limited to mouse, rat, cow, guinea pig, hamster, rabbit, cat, dog, goat, sheep, monkey, horse and chimpanzee.

As used herein, a substance of the present invention can include, but is not limited to, a protein, a drug, an antibody, an antibody fragment, an immunotoxin, a chemical compound, a protein fragment and a toxin. Examples of these substances include, but are not limited to anti-IL-13 antibodies, anti NK-T cell antibodies, anti-NK1.1 antibodies, anti-CD1 antibodies, IL-13Rα2-Fc, IL-13 Rα2, IL-13Rα, fragments of IL-13 Rα2, and fragments of IL-13 Rα. Extracellular fragments of IL-13Rα2 and IL-13Rα are also contemplated by the present invention as substances that are effective in treating or preventing colitis.

The IL-13Rα of the present invention can be the rat IL-13Rα or fragments of this receptor and the sequence for this receptor can be accessed on the GenBank database via Accession No. AY044251. This sequence is incorporated herein in its entirety by this reference. The IL-13Rα of the present invention can also be the mouse IL-13Rα or fragments of this receptor and the sequence for this receptor can be accessed on the GenBank database via Accession No. 580963. This sequence is incorporated herein in its entirety by this reference. The IL-13Rα of the present invention can also be the human IL-13Rα or fragments of this receptor and the sequence for this receptor can be accessed on the GenBank database via Accession No. U62858. This sequence is incorporated herein in its entirety by this reference.

The IL-13Rα2 of the present invention can also be the human IL-13Rα2 or fragments of this receptor and the sequence for this receptor can be accessed on the GenBank database via Accession No. NM_000640. This sequence is incorporated herein in its entirety by this reference. The IL-13Rα2 of the present invention can also be the mouse IL-13Rα2 or fragments of this receptor and the sequence for this receptor can be accessed on the GenBank database via Accession No. U65747. This sequence is incorporated herein in its entirety by this reference.

The antibodies of the present invention can be antibodies against human IL-13 (Dolganov, et al. "Coexpression of the interleukin-13 and interleukin-4 genes correlates with their physical linkage in the cytokine gene cluster on human chromosome 5q23-31" Blood 87 (8), 3316-3326 (1996)). The sequence of human IL-13 can be accessed on GenBank via Accession No. U31120 and is incorporated herein in its entirety by this reference. The antibodies of this invention can also be antibodies against mouse IL-13 (Brown, et al. "A family of small inducible proteins secreted by leukocytes are members of a new superfamily that includes leukocyte and fibroblast-derived inflammatory agents, growth factors, and indicators of various activation processes" J. Immunol. 142 (2), 679-687 (1989)). This sequence can be accessed on the GenBank database via Accession No. NM_008355 and is incorporated herein it its entirety by this reference.

By "treating" is meant that an improvement in the disease state, i.e., the inflammatory response of colitis, is observed and/or detected upon administration of a substance of the present invention to a subject. Treatment can range from a positive change in a symptom or symptoms of the disease to complete amelioration of the inflammatory response of colitis (e.g., reduction in severity or intensity of disease, alteration of clinical parameters indicative of the subject's condition, relief of discomfort or increased or enhanced function), as detected by art-known techniques. The methods of the present invention can be utilized to treat an established colitis. One of skill in the art would recognize that ulcerative colitis or indeterminate colitis refers to a condition of the colon characterized by a state of inflammation in which one or more of the following histological characteristics are detectable: a superficial inflammation characterized by the presence of epithelial cell loss and patchy ulceration, pronounced depletion of mucin producing-goblet cells, and reduction of the density of the tubular glands. In addition, in the lamina propia, a mixed inflammatory cell infiltrate consisting of lymphocytes and granulocytes (the latter consisting mostly of neutrophils and, to a lesser extent, eosinophils) associated with an exudation of cells into the bowel lumen is observed. Also, the submucosal level can display marked edema with few inflammatory cells, while in the outer muscle layer one of skill in the art would see little or no evidence of inflammation. See e.g. Boirivant et al. Journal of Experimental Medicine 188: 1929-

1939 (1998). Clinical symptoms can include, but are not limited to, diarrhea, rectal prolapse, weight loss, abdominal pain, dehydration and splenomegaly.

By "preventing" is meant that after administration of a substance of the present invention to a subject, the subject does not develop the symptoms of colitis (i.e. inflammation, diarrhea, rectal prolapse, weight loss, abdominal pain etc.) and/or does not develop colitis.

As used herein, modulation (e.g., maintenance, reduction or inhibition) of IL-13 activity means a change such as a decrease in IL-13 production, a decrease in IL-13 colitis-inducing effects, a decrease in cells producing IL-13 or a combination thereof. A reduction or inhibition in IL-13 activity can range from a decrease in IL-13 activity to complete amelioration of IL-13 activity. Maintenance of IL-13 activity means a maintenance of a steady state level of IL-13 without significant increase or decrease. One of skill in the art can utilize methods known in the art as well as those described in the Examples herein to measure and/or monitor IL-13 activity.

The present invention also provides a method of treating or preventing the inflammatory response of colitis in a subject comprising administering to the subject an effective amount of a substance that modulates (e.g. maintains, reduces or inhibits) NK-T cell activity.

Maintenance of NK-T cell activity means a maintenance of a steady state level of NK-T cell activity without significant increase or decrease. As used herein, reduction or inhibition of NK-T cell activity can be a decrease in the number of NK-T cells, a decrease in NK-T cell activation, a decrease in the interaction between NK-T cells and their respective ligands or any combination thereof. A reduction can range from a decrease in the number of NK-T cells to complete depletion of NK-T cells. Similarly, a reduction in the activation of NK-T cells can range from a decrease in the number of NK-T cells that are activated to inactivation of all NK-T cells. One of skill in the art would know which substance to utilize in order to inactivate NK-T cells or deplete them. For example, if one of skill in the art wished to deplete NK-T cells, anti-NK1.1 antibody would be utilized. Similarly, if inhibition of activation of NK-T cells is desired, an anti-CD1.1 antibody would be utilized. Therefore, antibodies that deplete NK-T cells as well as antibodies that prevent antigen presentation are contemplated to be an aspect of the invention.

Also contemplated by the present invention is a method of treating or preventing the inflammatory response of colitis in a subject comprising administering to the subject an effective amount of a first substance that reduces NK-T cell activity and an effective amount of a second substance that reduces IL-13 activity. The first and second substance can be administered together or separately to the subject in a ratio or combination determined to be effective in treating or preventing the inflammatory response of a colitis. The determination of such a ratio or combination amount is well within the scope of one of ordinary skill in the art.

The present invention also contemplates the treatment or prevention of the inflammatory response of colitis by the administration of a substance that reduces IL-13 activity with another therapeutic agent to a subject. Other therapeutic agents may include, but are not limited to, antibodies, such as an anti-IL-4 antibody, cytokines, or immunomodulatory agents. The invention also contemplates the treatment or prevention of the inflammatory response of colitis by the administration of a substance that reduces NK-T cell activity with another therapeutic agent to a subject.

Examples of these cytokines and immunomodulatory agents that can be employed in the methods of this invention include, but are not limited to, IVIG, antisera against lymphocyte membrane antigens (i.e. antithymocyte serum (ATS), antithymocyte globulin (ATG), antilymphocyte serum (ALS), antilymphocyte globulin (ALG), anti-CD3, anti-CD4, anti-CD8)), anti-TNFα, anti-IFNγ, antisense STAT4 oligonucleotides, anti-ICAM1, antisense ICAM-1 oligonucleotides, anti-CD40L, anti-CD25 (anti-Tag), and IL-10. Other cytokines and/or immunomodulators can be administered according to the methods of this invention both to treat an acute episode of disease or to maintain the subject's condition in a non-inflammatory state.

For the treatment and/or prevention methods of the present invention, including the combination therapies described above, the efficacy of administration as described herein in treating or preventing the inflammatory response of colitis in a subject can be determined by standard methods of evaluation of the particular signs, symptoms and objective laboratory tests for this disease, as known in the art. For example, 1) a subject's frequency or severity of recurrences is shown to be reduced, 2) the progression of the disease is shown to be stabilized, or 3) the need for use of other immunosuppressive medications is lessened, based on a comparison with an appropriate control group and knowledge of the normal progression of disease in the general population or the particular individual, then a particular treatment or prevention regimen will be considered efficacious.

The efficacy of combination therapy with any antibodies, immunosuppressive medications or immunomodulatory agents and substances that reduce IL-13 activity in preventing the inflammatory response of colitis can be determined by evaluating standard signs, symptoms and objective laboratory tests, as would be known to one of skill in the art, over time. The determination of who would be at risk for the development of colitis would be made based on current knowledge of the known risk factors for a particular disease familiar to a clinician in this field, such as a particularly strong family history of disease.

As mentioned above, the substance of the present invention can be an antibody. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequence of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab, scFv and the like, including hybrid fragments. Thus, fragments of the antibodies that retain the ability to bind their specific antigens are provided. For example, fragments of antibodies which maintain IL-13, CD1, CD1d, Vα14, Vα14Jα281, Vα24, Vα24Jα18, IL-13Rα, or IL-13Rα2 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which is hereby incorporated by reference herein in its entirety.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, scFv or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA,* 90:2551- 255 (1993); Jakobovits et al., Nature, 362:255-258 (1993); Bruggemann et al., *Year in Immunol.,* 7:33 (1993)). Human antibodies can also be produced in phage display libraries (Hoogenboom et al., *J. Mol. Biol.,* 227:381 (1991); Marks et al., *J. Mol. Biol.,* 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985)0; Boerner et al., *J. Immunol.,* 147(1):86-95 (1991)).

The present invention further provides a hybridoma cell that produces the monoclonal antibody of the invention. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA,* 81:6851-6855 (1984)).

Monoclonal antibodies of the invention may be prepared using hybridoma methods, such as those described by Kohler and Milstein, *Nature,* 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises IL-13, CD1, CD1d, Vα14, Vα14Jα281, Vα24, Vα24Jα18, IL-13Rα, or IL-13Rα2 or a fragment thereof. Traditionally, the generation of monoclonal antibodies has depended on the availability of purified protein or peptides for use as the immunogen. More recently DNA based immunizations have been employed to elicit strong immune responses and generate monoclonal antibodies. In this approach, DNA-based immunization is used, wherein DNA encoding a portion of IL-13, CD1, CD1d, Vα14, Vα14Jα281, Vα24, Vα24Jα18, IL-13Rα, or IL-13Rα2 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma.* 1998 Dec; 17(6): 569-76; Kilpatrick K E et al. High-affinity monoclonal antibodies to PED/PEA-15 generated using 5 microg of DNA. *Hybridoma.* 2000 Aug; 19(4):297-302, which are incorporated herein by referenced in full for the the methods of antibody production) and as described in the examples.

An alternate approach to immunization with either purified protein or DNA is to use antigen expressed in baculovirus. The advantages to this system include ease of generation, high levels of expression, and post-translational modifications that are highly similar to those seen in mammalian systems. Use of this system involves expressing domains of IL-13, CD1, CD1d, Vα14, Vα14Jα281, Vα24, Vα24Jα18, IL-13Rα, or IL-13Rα2 antibody as fusion proteins. The antigen is produced by inserting a gene fragment in-frame between the signal sequence and the mature protein domain of the IL-13, CD1, CD1d, Vα14, Vα14Jα281, Vα24, Vα24Jα18, IL-13Rα, or IL-13Rα2 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice* Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.,* 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against IL-13, CD1, CD1d, Vα14, Vα14Jα281, Vα24, Vα24Jα18, IL-13Rα, or IL-13Rα2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane *Antibodies, A Laboratory Manual* Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the invention or substituted for the variable domains of one antigen-combining site of an antibody of the invention to create a chimeric bivalent antibody comprising one antigen-combining site having specificity for IL-13, CD1, CD1d, Vα14, Vα14Jα281, Vα24, Vα24Jα18, IL-13Rα, or IL-13Rα2 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to liNK-Two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant. *Synthetic Peptides: A User Guide.* W. H. Freeman and Co., N.Y. (1992); Bodansky and Trost., Ed. (1993) *Principles of Peptide Synthesis.* Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen et al., *Biochemistry,* 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science,* 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al. (1992) *FEBS Lett.* 307: 97-101; Clark-Lewis et al., *J. Biol. Chem.,* 269:16075 (1994); Clark-Lewis et al., *Biochemistry,* 30:3128 (1991); Rajarathnam et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton et al., *Techniques in Protein Chemistry* IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with IL-13, CD1, CD1d, Vα14, Vα14Jα281, Vα24, Vα24Jα18, IL-13Rα, or IL-13Rα2. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller et al. *Nucl. Acids Res.* 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. (*Antibodies, A Laboratory Manual*. Cold Spring Harbor Publications, New York, (1988)), for a description of immunoassay formats and conditions that could be used to determine selective binding. The binding affinity of a monoclonal antibody can, for example, be determined by the Scatchard analysis of Munson et al., (*Anal. Biochem.*, 107:220 (1980).

Also provided is an antibody reagent kit comprising containers of the monoclonal antibody or fragment thereof of the invention and one or more reagents for detecting binding of the antibody or fragment thereof to IL-13, CD1, CD1d, Vα14, Vα14Jα281, Vα24, Vα24Jα18, IL-13Rα, or IL-13Rα2 receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

Administration of Antibodies

The antibodies described herein of the invention are preferably administered to a subject in a pharmaceutically acceptable carrier. Suitable carriers and their formulations are described in *Remington: The Science and Practice of Pharmacy* ((19th ed.) ed. A. R. Gennaro, Mack Publishing Company, Easton, Pa. 1995). Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), intrarectally or by other methods such as infusion that ensure its delivery to the bloodstream in an effective form. Local or intravenous injection is preferred.

Effective dosages and schedules for administering antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Following administration of a substance for treating, inhibiting, or preventing inflammation of colitis, the efficacy of the therapeutic substance can be assessed in various ways well known to the skilled practitioner. For instance, one of ordinary skill in the art will understand that a substance of the invention is efficacious in treating or inhibiting inflammation of an established colitis in a subject by observing that the substance reduces inflammation or prevents a further increase in inflammation. Inflammation can be measured by methods that are known in the art, for example, using tissue biopsies to assess tissue damage or antibody assays to detect the presence of inflammatory cytokines in a sample (e.g., bodily fluids, but not limited to, blood) from a subject or patient, or by measuring the cytokine levels in the patient. Efficacy of the treatment may also be determined by measuring the number of NK-T cells in the subject (e.g. in the colon or peripheral blood) with inflammation from colitis. A treatment that inhibits an initial or further increase in NK-T cells or IL-13 levels in a subject or patient with inflammation of an established colitis, or that results in a decrease in the number of NK-T cells or IL-13 levels in a subject or patient with inflammation of an established colitis, is an efficacious treatment.

The substances of the invention may be administered prophylactically to patients or subjects who are at risk for having inflammatory bowel disease or who have been newly diagnosed with inflammatory bowel disease. In subjects who have been newly diagnosed with inflammatory bowel disease but who have not yet displayed an established colitis or the inflammatory response of an established colitis (as measured by biopsy or other assays for detecting the inflammation due to colitis) in blood or other body fluid, efficacious treatment with an substance of the invention partially or completely inhibits the appearance of colitis symptoms and/or colitis.

Nucleic Acid Approaches for Delivery

The substances of the present invention, including antibodies and antibody fragments of the invention can also be administered in vivo and/or ex vivo to patients or subjects as a nucleic acid preparation (e.g., DNA or RNA) that encodes a substance, such as an antibody or antibody fragment, such that the patient's or subject's own cells take up the nucleic acid and produce and secrete the encoded substances, such as an antibody or antibody fragment.

In the methods described above which include the administration and uptake of exogenous DNA into the cells of a subject (i.e., gene transduction or transfection), the nucleic acids of the present invention can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOPECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996) to name a few examples. This invention can be used in conjunction with any of these or other commonly used gene transfer methods.

As one example, if the antibody-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Pharmaceutically Acceptable Carriers

The substances of the present invention, including antibodies, can be used therapeutically in combination with a pharmaceutically acceptable carrier. By "pharmaceutically acceptable" is meant a material that is not biologically or otherwise undesirable, i.e., the material may be administered to a subject, along with the substance, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including rectally, intranasally), orally, by inhalation, or parenterally, for example by intravenous drip, subcutaneous, intraperitoneal or intramuscular injection. The disclosed substances can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Screening Methods

Also provided by the present invention is a method of screening a substance for effectiveness in reducing the inflammatory response of colitis by modulating IL-13 activity comprising: a) obtaining an animal having colitis; b) administering the substance to an animal; and assaying the animal for an effect on IL-13 activity which results in the reduction of the inflammatory response of the colitis, thereby identifying a substance effective in reducing the inflammatory response of colitis by modulating IL-13 activity.

The ability of a substance to reduce the colitis inducing effect of IL-13 can be determined by evaluating the histological and clinical manifestations, as set forth above, of the animal with colitis before and after administration of the substance of interest and quantitating the amount of reduction of the inflammation.

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. The hapten reagent can be, but is not limited to, oxazolone (4-ethoxymethylene-2-phenyl-2-oxazolin-5-one).

The present invention also provides a method of screening a substance for effectiveness in reducing the inflammatory response of colitis by modulating NK-T cell activity comprising: a) obtaining an animal having colitis; b) administering the substance to an animal; and c) assaying the animal for an effect on NK-T cell activity which results in the reduction of the inflammatory response of the colitis, thereby identifying a substance effective in reducing the inflammatory response of colitis by modulating NK-T cell activity.

The ability of a substance to reduce the colitis inducing effect of NK-T cells can be determined by evaluating the histological and clinical manifestations, as set forth above, of the animal with colitis before and after administration of the substance of interest and quantitating the amount of reduction of the inflammation. One of skill in the art can also quantitate the number of NK-T cells by methods standard in the art and those described herein in order to determine if the substance reduces the number of NK-T cells, as determined in lamina propia cells or PBM.

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. The hapten reagent can be, but is not limited to, oxazolone (4-ethoxymethylene-2-phenyl-2-oxazolin-5-one).

The present invention also provides a method of screening for a substance effective in preventing the inflammatory response of colitis by modulating IL-13 activity comprising: a) administering the substance to an animal susceptible to colitis: b) subjecting the animal to treatment that will induce an inflammatory response; and c) assaying inflammatory tissue cells from the animal for an amount of secretion of IL-13, whereby a decrease or lack of increase in the amount of IL-13 in the inflammatory tissue cells of the animal as compared to an increase in the amount of IL-13 in a control animal having colitis in the absence of the substance identifies a substance that is effective in preventing the inflammatory response of colitis by modulating IL-13 activity.

The methods of measuring the amount of IL-13 in inflammatory tissue include, but are not limited to, ELISA, PCR, FACS analysis, reverse-transcriptase-polymerase chain reaction and ELISPOT, Northern blots, Southern blots, and Western blots.

Also provided by the present invention is a method of screening for a substance effective in preventing the inflammatory response of colitis by modulating NK-T cell activity comprising: a) administering the substance to an animal susceptible to colitis; b) subjecting the animal to treatment that will induce an inflammatory response; and c) assaying the animal for an effect on NK-T cell activity, whereby a decrease or lack of increase in NK-T cell activity in the inflammatory tissue cells of the animal as compared to an increase in NK-T cell activity in a control animal having colitis in the absence of the substance identifies a substance that is effective in preventing the inflammatory response of colitis by modulating NK-T cell activity.

One of skill in the art can utilize methods standard in the art as well as those described in the Examples to quantitate NK-T cells in inflammatory tissues.

Therapeutic Uses

The substances of the present invention can be delivered at effective amounts or concentrations. An effective concentration or amount of a substance is one that results in treatment or prevention of the inflammatory response of colitis. One skilled in the art would know how to determine an effective concentration or amount according to methods known in the art, as well as provided herein. One of skill in the art can utilize in vitro assays to optimize the in vivo dosage of a particular substance, including concentration and time course of administration. The dosage ranges for the administration of the substances are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

For example, to evaluate the efficacy of treatment of humans with a disorder characterized by colitis, such as for example, ulcerative colitis, with a substance that modulates IL-13 activity, the following studies can be performed. Patients with active inflammation of the colon and/or the terminal ileum who have failed standard medical therapy, which can include prednisone and/or other immunomodulators known in the art (parenterally or orally) for control of the disorder can be selected. Drug efficacy can be monitored via colonoscopy. Patients can be randomized to two different protocols. In one protocol, subjects can remain on initial medication and in the second protocol, subjects can have their medication tapered after receiving the substance that modulates IL-13 activity.

In one embodiment, treatment can consist of either a single dosage of 1 mg to 20 mg/kg of body weight of a substance that modulates IL-13 activity and/or NK-T cell activity. In one example, an antibody to IL-13 is infused over a two hour period or a weekly dosage of 1 mg to 20 mg/kg of body weight of antibodies to IL-13 infused each time over a two hour period until symptoms of colitis subside. The blood pressure, pulse and temperature of the subjects can be monitored prior to and at 30 minute intervals during the two hour infusion period. Subjects can be given a laboratory evaluation consisting of a complete blood count (CBC) with differential, platelet count, SMA-18 chemistry profile, erythrocyte sedimentation rate (ESR) and a C-reactive protein assay at 1) the time of anti-IL-13 infusion; 2) 24 hours after infusion; 3) 72 hours after infusion; 4) two weeks after the last infusion; 5) four weeks after the last infusion; (6) six weeks after the last infusion; and 7) eight weeks after the last infusion. Similarly, an antibody that modulates NK-T cell activity can be administered according to the same protocol.

Subjects can also undergo routine colonoscopy with video surveillance at the time of the infusion of a substance that modulates IL-13 activity and/or NK-T cell activity and again at two, four, six and eight weeks after the last infusion. Additionally, serum samples from the subjects can be assayed by ELISA for IL-13 activity and/or NK-T cell activity levels to monitor drug efficacy. Also, tissue biopsy samples obtained during colonoscopy can be cultured for purified, isolated lamina propia cells and assayed as well. Purified PBM can also be isolated, cultured and assayed.

Compositions Identified by Screening with Disclosed Compositions/Combinatorial Chemistry/Computer Assisted Drug Design The disclosed compositions, such as IL-13, CD1, CD1d, V$\alpha$14, V$\alpha$14J$\alpha$281, V$\alpha$24, V$\alpha$24J$\alpha$18, IL-13R$\alpha$, or IL-13R$\alpha$2 or fragments thereof, can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation of the target molecule's function. The molecules identified and isolated when using the disclosed compositions, such as IL-13, CD1, CD1d, V$\alpha$14, V$\alpha$14J$\alpha$281, V$\alpha$24, V$\alpha$24J$\alpha$18, IL-13R$\alpha$, or IL-13R$\alpha$2, are also disclosed. Thus, the products produced using the molecular modeling approaches that involve the disclosed compositions, such as, IL-13, CD1, CD1d, V$\alpha$14, V$\alpha$14J$\alpha$281, V$\alpha$24, V$\alpha$24J$\alpha$18, IL-13R$\alpha$, or IL-13R$\alpha$2, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will liNK-To the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol, Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lund.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter binding specificity for IL-13 or any other composition described herein.

Compositions with Similar Functions

It is understood that the compositions disclosed herein have certain functions, such as binding IL-13, CD1, CD1d, Vα14, Vα14Jα281, Vα24, Vα24Jα18, IL-13Rα, or IL-13Rα2. Disclosed herein are certain structural requirements for performing the disclosed functions, and it is understood that there are a variety of structures which can perform the same function which are related to the disclosed structures, and that these structures will ultimately achieve the same result, for example inhibition of NK-T cells or IL-13 production, secretion, or action.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

In the present invention, a mouse model of oxazolone colitis was utilized to study Th2 cytokine production. In the Th2 model of oxazolone colitis, colitis is induced by the intra-rectal administration of the haptenating agent oxazolone in an ethanol vehicle. In this colitis, initial toxic effects of the inducing agent lead to a flooding of the lamina propria with bacterial antigens and thus the induction of an immune response that leads to further inflammation. The latter is driven by the production of Th2 cytokines since the inflammation is characterized by increased IL-4 and IL-5 secretion and the inflammation can be ameliorated by the administration of anti-IL-4 (Boirivant et al., 1998).

The present invention provides the surprising result that oxazolone colitis is mediated by NK-T cells capable of producing large amounts of Th2 cytokines when stimulated by either anti-CD3 or αGalCer. Initially, this consists of IL-4 secretion, which is rapidly superceded by IL-13 secretion. This IL-13 response originates from NK-T cells responding to CD1-mediated antigen presentation and appears to be a key component of the inflammation, as neutralization of IL-13 prevents development of oxazolone colitis. Given the resemblance of oxazolone colitis in mice to ulcerative colitis in humans, these data indicate that similar treatment of human inflammatory disease would be effective.

Mice and in vivo Treatment Protocols

Male C57B1/10 mice were obtained from a breeding facility maintained by the National Cancer Institute (NCI, Bethesda, Md.) and were housed under specific pathogen free (SPF) conditions. 5 to 7 week old mice were used for all experiments. B6x129Sv-CD1 KO mice were received from Exley/Balk (Cui et al., 1997; Smiley et al., 1997), C57B1/6-Jα281 KO mice were a generous gift from Dr. Taniguchi (Cui et al., 1997) and bred at the animal facility at Brigham and Women's Hospital, Harvard Medical School, Boston, Mass. Oxazolone (4-Ethoxymethylene-2-Phenyl-2-Oxazoline-5-One) was obtained from Sigma-Aldrich (St. Louis, Mo.). In order to presensitize mice a 2×2 cm field of the abdominal skin was shaved and 200 µl of a 3% (w/v) solution in 100% ethanol applied. 5 days after presensitization mice were rechallenged intra-rectally with 150 µl 1% Oxalone in 50% ethanol or only 50% ethanol (i.e. vehicle) under general anesthesia with isoflurane (Baxter, Deerfield, Ill.). Intra-rectal injection was administered with a polyurethane umbilical catheter (Sherwood, St. Louis, Mo.). Neutralization of IL-13 in vivo was performed with IL-13Rα2-Fc. Mice received 5×200 µg of control protein or IL-13Rα2-FcN starting on the day before presensitization i.v. and then every other day i.p. Depletion of NK1.1+ cells was achieved by injecting 250 µg anti-mouse NK1.1 monoclonal antibodies (clone PK136) i.v. 48 h before and after sensitization. Control mice received mouse IgG2a. FACS analysis of spleenocytes from treated animals showed that NK as well as NK-T cells were completely depleted. Antigen presentation by CD1 molecules was blocked in vivo with anti-mouse CD1.1 (clone 20H2, gift from A. Bendelac) Mice were injected with 1 mg antibody every 2 days.

Histology

Mice were euthanized 5 days after induction of colitis. The colons were removed and segments fixed in formalin (Fisher, Fair Lawn, N.J.). After paraffin embedding 5 µm sections were cut and stained with Hematoxylin/Eosin (Lerner, New Haven, Conn.).

Cell Isolation and Cytokine Production

Spleenocytes (SPC), mesenteric lymph node cells (MLNC) or lamina propria cells were isolated on day 2 or day 7 after colitis induction. Cells were isolated as described in detail in Current Protocols of Immunology (Scheiffele, 2002). In brief, LPMC were isolated after removal of epithelial cells by incubation of colon strips in HBSS/2.5 mMEDTA. Mononuclear cells were released by digesting the tissue in ISCOVES media supplemented with 10% FCS, 200 U/ml collagenase (Roche, Indianapolis, Ind.), 10 µg/ml DNAse 1 (Roche) and 1 µg/ml Gentamicin (BioWhittaker, Walkersville, Md.). Finally, leukocytes were separated from epithelial cells by centrifugation in a PERCOLL gradient (Amersham, Piscataway, N.J.) of 33% and 66%. MLN cells and spleenocytes were isolated by grinding the tissue in a petri dish and filtering the cell suspension through a 40 µm mesh. Spleen cells were treated with ACK lysis buffer to lyse red blood cells (Biosource, Camarillo, Calif.). Initially CD3 cells were isolated with mouse T-cell selection columns (R&D, Minneapolis, Minn.) according to the manufacturer's instructions. Purified CD4 cells were positively selected with CD4-beads and MACS mini columns (Miltenyi, Auburn, Calif.) according to the manufacturer's instructions. Cells were cultured in RPM1640 supplemented with 10% FCS, 20 m MHEPES, 5% NCTC, 2 mM Glutamine, 50 µg/ml Penicillin/Streptomycin, 50 µg/ml Gentamicin, 50 µM 2-mercaptoethanol, and 50U rhu IL-2. T cells were stimulated in vitro with plate bound anti-CD3 (10 µg/ml 2C11, Pharmingen, San Diego, Calif.) and soluble anti-CD28 (1 pg/ml clone 37.51, Pharmingen). To stimulate lymphocytes with αGalCer a fibroblast cell line (L-929) transfected with mouse CD1 as antigen presenting cells was used. CD1 transfected ("LCD1") or untransfected ("LC") were a kind gift by Dr W. Paul (Chen and Paul, 1997). L-cells were treated for 1.5 h with Mitomycin C and seeded at $1\times10^5$ cells/ml. αGalactosyl-Ceramide (αGalCer;Kirin, Tokyo, Japan) or vehicle was added at 100 ng/ml. Lymphocyte concentration was generally $1\times10^6$ cells/ml. After 48 h culture, supernatants were harvested and stored at −20° C. until further analysis. IL-4 and IL-5 were measured with OptEIA ELISA sets from Pharmingen. IL-13 was measured with a Quantikine M ELISA kit from R&D (Minneapolis, Minn.).

FACS Analysis

Cells were stained with antibodies to CD3 (2C11), CD4 (RM4-5), NK1.1 (PK136), Ly49C (5E6), Ly6C (AL-21), and DX5 after incubation with FcBlock (2.4G2) (all BD Pharmingen). Surface staining was analyzed on a FACScanner (Becton-Dickinson, Mansfield, Mass.). Relative numbers were calculated with CellQuest software after gating on living lymphocytes in the scatter diagram.

Figure 2:
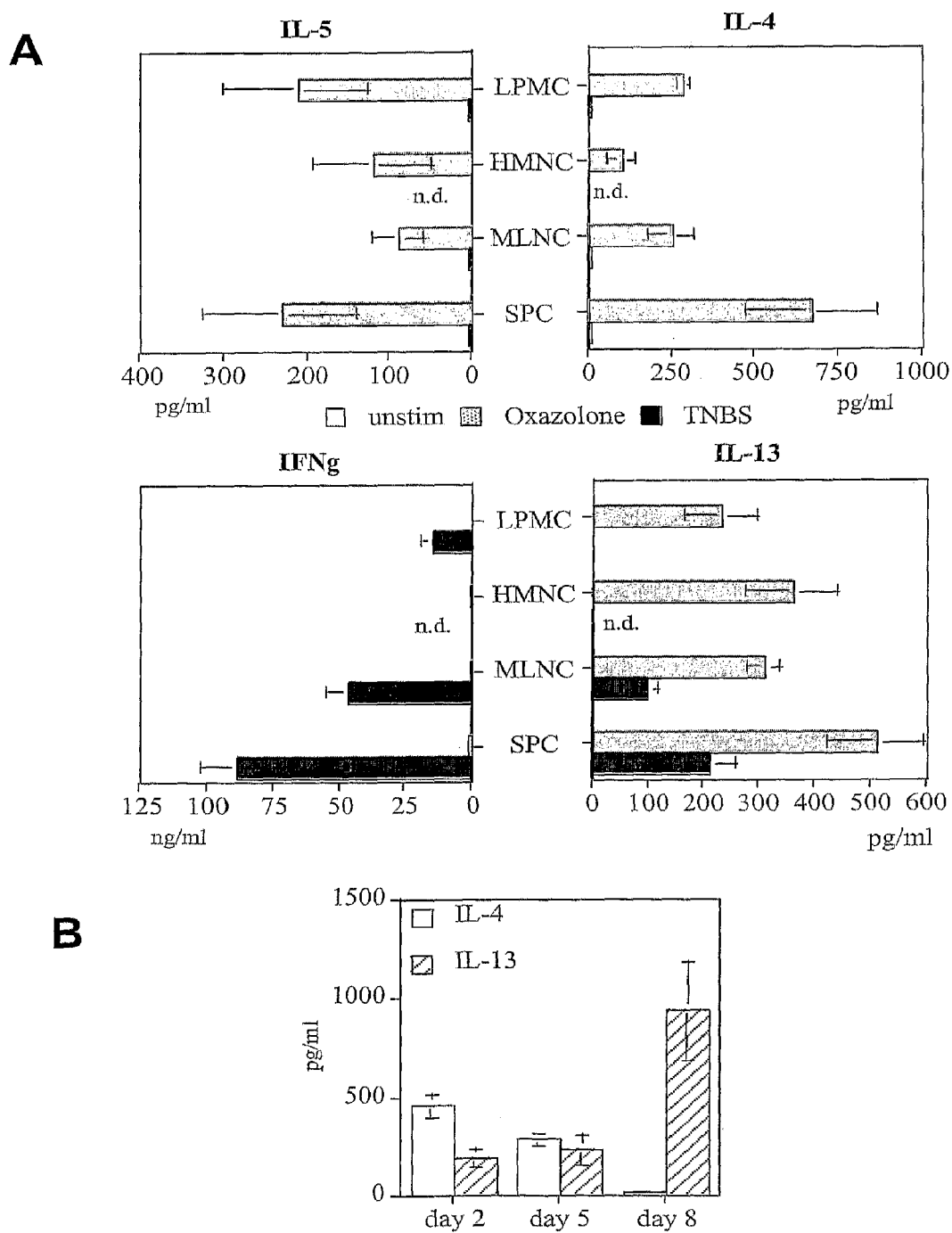
FIGS. 2A-B show cytokine production from lymphocytes from mice with oxazolone colitis. (A) Lamina propria mononuclear cells (LPMC), hepatic mononuclear cells (HMNC), mesenteric lymph node cells (MLNC) and spleenocytes (SPC) were isolated on day 5 after induction of oxazalone colitis (gray) or TNBS (black) colitis and stimulated in vitro for 48 h with plate-bound anti-CD3 and anti-CD28. Cytokine concentrations were measured in supernatants by ELISA. (B) LPMC were isolated on day 2, 5 or 8 after induction of oxazalone colitis. LPMC were stimulated as above, and the concentrations of IL-4 (open) and IL-13 (striped) measured in the supernatants.

Epicutaneous Presensitization and Intrarectal Rechallenge with Oxazolone Leads to Chronic Progressive Oxazolone Colitis Associated with Th2 Cytokine Production To obtain a more long-lived, chronic inflammatory response on the oxazolone colitis mouse model, mice were presensitized with 3% oxazolone by skin painting 5 days before rectal challenge and then injected intrarectally 1% oxazalone to induce colitis. As shown in FIG. 1A, only pre-sensitized mice developed colitis and progressive weight loss, whereas naïve animals did not develop any inflammation. In addition, as shown in FIG. 1B, the colitis induced in this case led to a chronic progressive wasting and weight loss so that after 7-10 days most animals had lost 40% of their initial body weight and were moribund. Histological examination of the colon at days 7-10 showed a massive bowel wall edema and infiltration by leukocytes. The superficial layers of the mucosa show dense infiltrations with small polynuclear granulocytes and large ulcerations interrupting the layer of enterocytes are present. As shown in FIG. 1D+E, this histopathological picture is similar to that seen in human ulcerative colitis suggesting that a similar pathological mechanism contributes to tissue damage in both inflammations. Finally, as shown in FIG. 2A, mononuclear cells isolated from the lamina propria (LPMC), mesenteric lymph nodes (MLNC), or spleen (SPC), and then stimulated with anti-CD3/anti-CD28 in vitro produced large amounts of Th2 cytokines (IL-4, IL-5, IL-13) but only low levels of IFN-γ. On the contrary LPMC isolated from mice with TNBS colitis produce undetectable levels of IL-4 and IL-5, and only low levels of IL-13, but very high amounts of TNFα.

Figure 3:
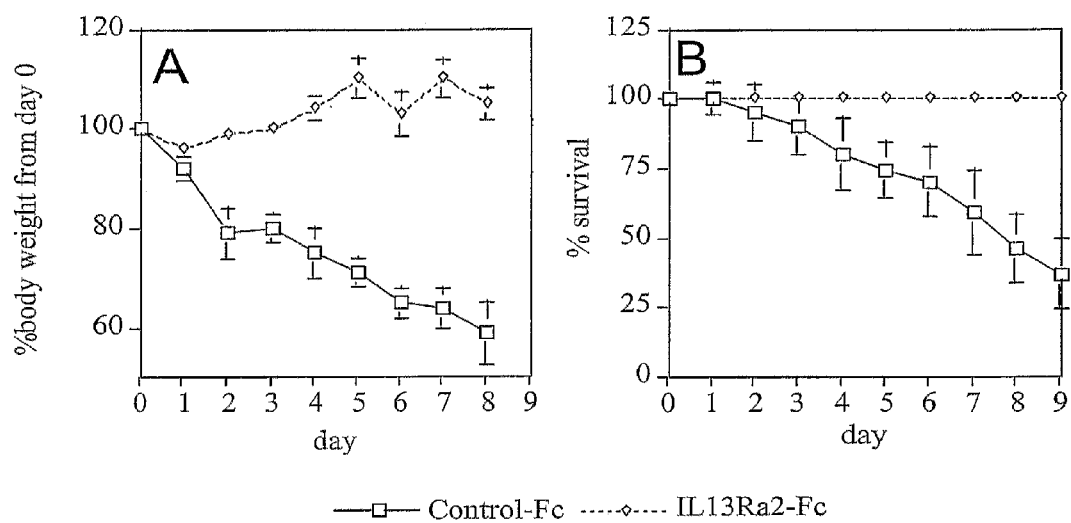
FIGS. 3A-B show that neutralization of IL-13 prevents induction of oxazolone colitis. (A) Weight loss and (B) mortality from mice with oxazolone colitis treated with IL13Rα2-Fc (diamonds) or control-protein (squares).

IL-13 Production in Oxazolone Colitis Increases During the Course of Inflammation and is Essential for the Induction of the Colitis IL-4 production by LPMC isolated at different time points during the course of oxazolone colitis gradually decreased. In contrast, IL-13 production by LPMC (as well as ML MC or spleen MC) during the same timeframe increased (FIG. 2B). This phenomenon has been observed in other animal models mediated by Th2 cells (Minty et al., 1997; Urban et al., 1998). To establish a pathogenic role for IL-13 in oxazolone colitis, IL-13 was neutralized by in vivo administration of IL-13Rα2 fused to the Fc portion of human IgG1 (IL-13Rα2-Fc) at the time of intra-rectal oxazolone administration. The α2 chain of the IL-13 receptor has a 100 fold higher affinity to IL-13 than the α1 chain, but only the latter transmits an intracellular signal after engagement. The IL-13Rα2-Fc fusion protein binds IL-13 and has been shown to neutralize IL-13 boactivity in vivo (Donaldson et al., 1998). As shown in FIG. 3, mice treated with IL-13Ra2-Fc were protected from induction of oxazolone colitis: after an initial transient weight loss similar to that seen with ethanol alone, they regained their initial body weight by day 3 and on day 5 colonic histology was indistinguishable from that of mice that were given ethanol alone.

NK1.1-Positive Cells are Essential for the Induction of Oxazolone Colitis

Figure 4:
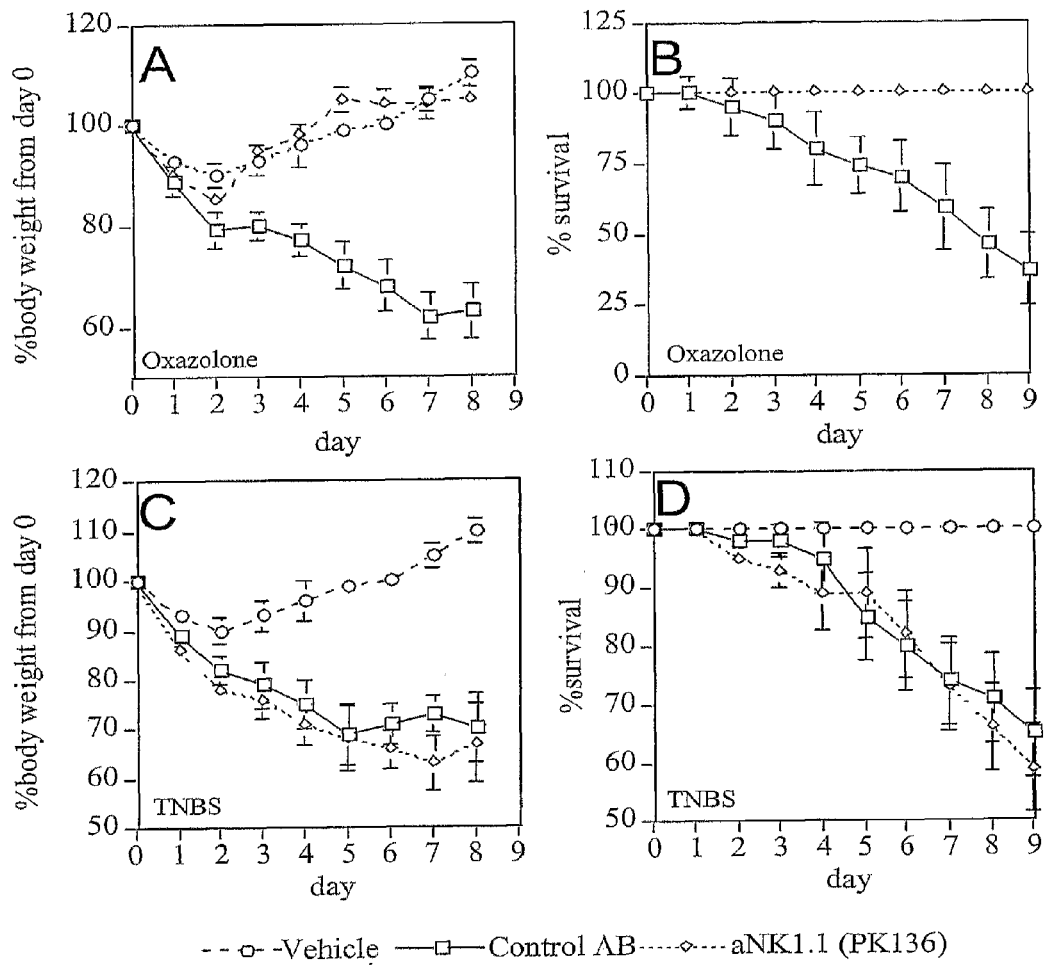
FIGS. 4A-D show that depletion of NK1.1 lymphocytes protects mice from oxazolone colitis but not TNBS colitis. Weight loss (A+C) and mortality (B+D) after induction of oxazalone colitis (A+B) or TNBS colitis (C+D) or injection of vehicle (ethanol; circles). Mice were injected wih control antibody (squares) or depleted of NK1.1 cells with PK136 (diamonds).

As alluded to above, mononuclear cells isolated from mice with oxazolone colitis produce increased amounts of IL-13 in vitro when stimulated with anti-CD3 and anti-CD28. However, when these mononuclear cells were purified by a negative selection column to enrich for CD3-positive cells, this stimulation led to greatly decreased IL-13 production (not shown). Since the selection column contains glass beads coated with anti-mouse IgG, it retains cells that express Fc-receptors (CD16 or CD32) and are coated with immunoglobulins; thus it was possible that IL-13 production by anti-CD3-stimulated LPMC in oxazolone colitis requires a Fc-receptor-positive cell. In addition to mast cells and B-lymphocytes, NK and NK-T cells express CD16 (Koyasu, 1994) and are capable of producing M-13 (Terabe et al., 2000). To investigate if either of the latter two (and more likely) cell types are involved mice were depleted of NK1.1 cells by repeated injection of monoclonal anti-NK1.1 antibody (PK136) before challenge with oxazolone. Such treatment depleted all NK and NK-T cells, as determined by DX5 and NK1.1 staining of splenocytes. As shown in FIG. 4A+B, it was found that depleted mice did not develop weight loss or macroscopic/microscopic evidence of colonic inflammation and did not manifest increased Th2 cytokine production after intra-rectal challenge with oxazolone.

In further studies to determine if this pathogenic role for NK1.1 positive cells is specific for oxazolone colitis, NK1.1-depleted C57Bl/10 mice were compared with untreated C57Bl/10 mice in their susceptibility to TNBS-colitis, a Th1 model of colitis resembling human Crohn's disease. As shown in FIG. 4C+D, depletion of NK1.1+ cells does not significantly influence weight loss or mortality of mice with TNBS colitis, and notably, there was a trend to higher weight loss in depleted mice. These results suggest that cells bearing NK1.1 in the mucosa play, if anything, an inhibitory role for the induction of a Th1 inflammation in TNBS-colitis, an effect previously noted in other models of Th1-mediated intestinal inflammations (Saubermann et al., 2000).

CD1 Antigen Presentation is Required for the Induction of Oxazolone Colitis

Figure 5:
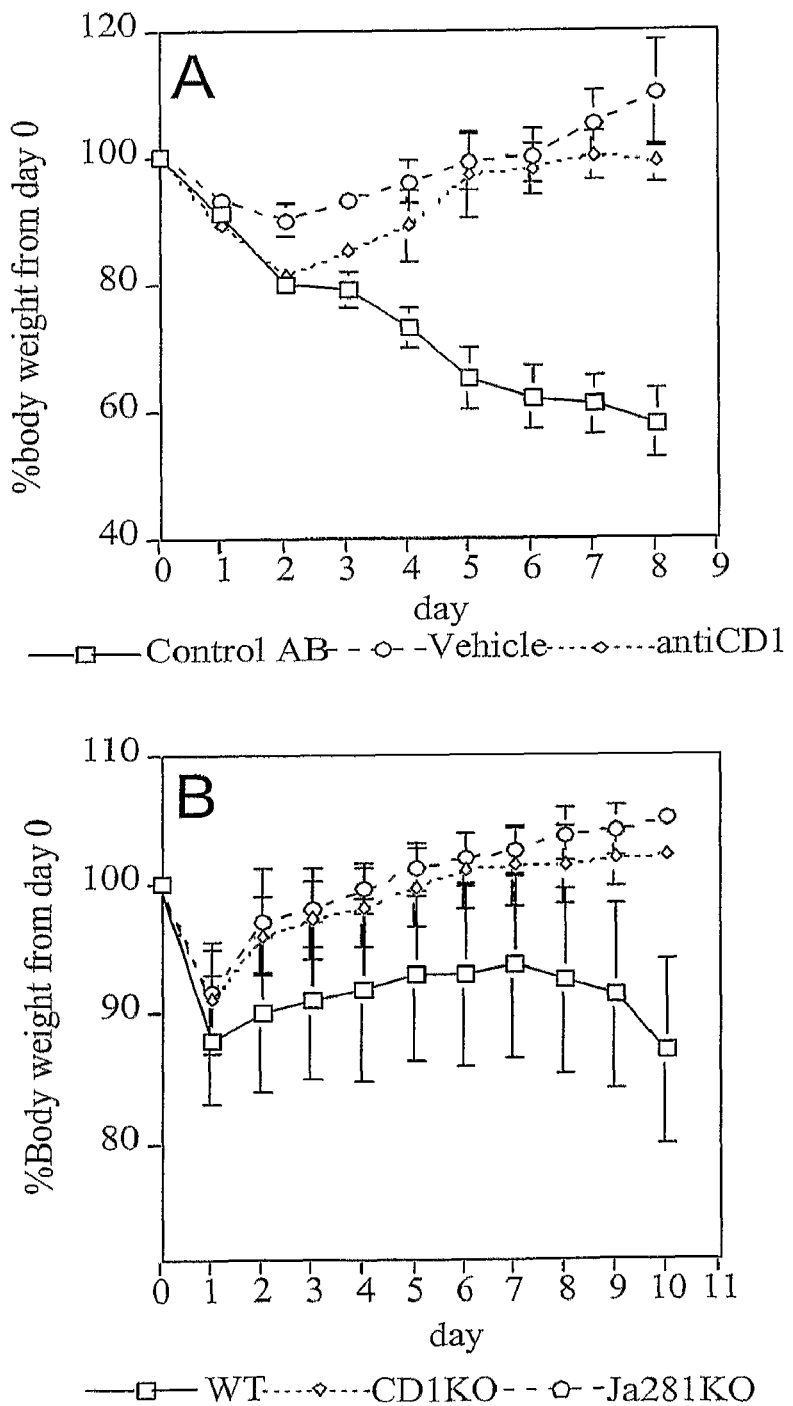
FIGS. 5A-B show CD1 antigen presentation and that Jα281 NK-T cells are essential for induction of oxazalone colitis. (A) Weight loss of mice after intra-rectal injection of vehicle (circles) or oxazalone after i.v. injection of blocking CD1 antibodies (20H2; diamonds) or control antibody (squares). (B) Weight loss after induction of oxazalone colitis of CD1KO mice (diamonds), Jα281KO mice (circles) and wildtype mice (squares).

Whereas the above studies show that oxazolone colitis is mediated by NK1.1-positive cells they do not provide information on whether the latter cells are NK cells or NK-T cells, as NK1.1 is present on both of these cell types. To address this issue, whether oxazolone colitis was affected by blockade of antigen presentation by CD1 molecules which affects activation of NK-T cells but not the activation of NK cells was examined. This was accomplished by administration of a monoclonal anti-CD1 antibody that has been shown to block CD1 in vivo without depleting NK-T cells and without affecting antigen-presentation by MHC class II (Park et al., 1998). As shown in FIG. 5, administration of this antibody at the time of intra-rectal oxazolone administration prevented development of oxazolone colitis.

As shown in FIG. 5B, these results were confirmed with studies of CD1-KO mice, in which it was shown that intra-rectal administration of oxazolone to pre-sensitized mice do not develop colitis nor a colonic Th2 response. Despite the absence of NK-T cells the CD1-KO mice have been shown to be fully capable of mounting Th2 responses (Smiley et al., 1997). Thus, this result cannot be attributed to an intrinsic failure of the CD1 KO to mount a Th2 response.

Finally it was found that Jα281 KO mice are resistant to the induction of oxazalone colitis (FIG. 5B). While most CD1 restricted NKT cells utilize the canonical Vα14Jα281TCR, some results suggested the existence of NKT cells with other TCRs. These "atypical" NKT cells are present in the Jα281-KO mouse, but proved to be insufficient to induce an inflammatory response. Taken together, data from the antibody-treated and KO mice show that oxazolone colitis is dependent on the induction of T cells by CD 1-restricted antigens and that the T cells are NK1.1+Jα281+CD16+CD4+cells.

NK-T Cells Undergo Expansion During Oxazolone Colitis

In further studies whether or not NK-T cells infiltrate the lamina propria of mice with oxazalone colitis was determined. However, this goal is made difficult by the fact that whereas NK1.1 is a frequent marker of NK-T cells, T cells with NK-T cell function have also been identified in the NK1.1-negative population. In addition, most NK-T cell markers are dependent on the levels of cell activation. Thus, NK-T cells lose their expression of NK1.1 upon activation (Chen and Paul, 1997) and another NK/NK-T cell marker, Ly49C, is upregulated in activated NK-T cells. Beside activation, NKT cells from different tissues co-express different surrogate markers of NK cell function together with the TCR. With these limitations in mind, it was found that during the course of oxazolone colitis total lymphocyte numbers expand significantly in the lamina propria (~10-fold), liver (~6 fold), mesenteric lymph nodes (~50 fold) and spleen (~2 fold). Moreover, in the lamina propria and in the liver the relative number of NK-T cells expands in relation to other cell populations. Thus, in the lamina propria from untreated mice 7% (NK1.1) or 0.4% (Ly49C) of the T cells co-express an NKT cell marker. After induction of oxazolone colitis 21% of the infiltrating T-cells are NK1.1 positive and 34% are Ly49C positive. In the liver, where the highest percentage of NKT cells can be found, NK1.1 expression on CD3 positive cells increases from 9.9% to 48% of cells, while Ly49C expression is low. For unknown reasons, NKT cells are absent from mesenteric lymph nodes even after colitis induction: at this site, less than 1% of the cells can be identified as NKT cells. Finally, in the spleen of untreated mice 3.1% of CD3-positive cells are NK1.1+, and after induction of oxazolone colitis 5.1% become NK1.1 positive, while the number of Ly49C30 cells increases from 0.6% to 28%. To summarize these findings, T cells with surrogate markers of NKT cell function expand in the lamina propria, the liver and the spleen.

CD4+ NK-T Cells Produce IL-13 in Response to CD1 Antigen Presentation

Figure 6:
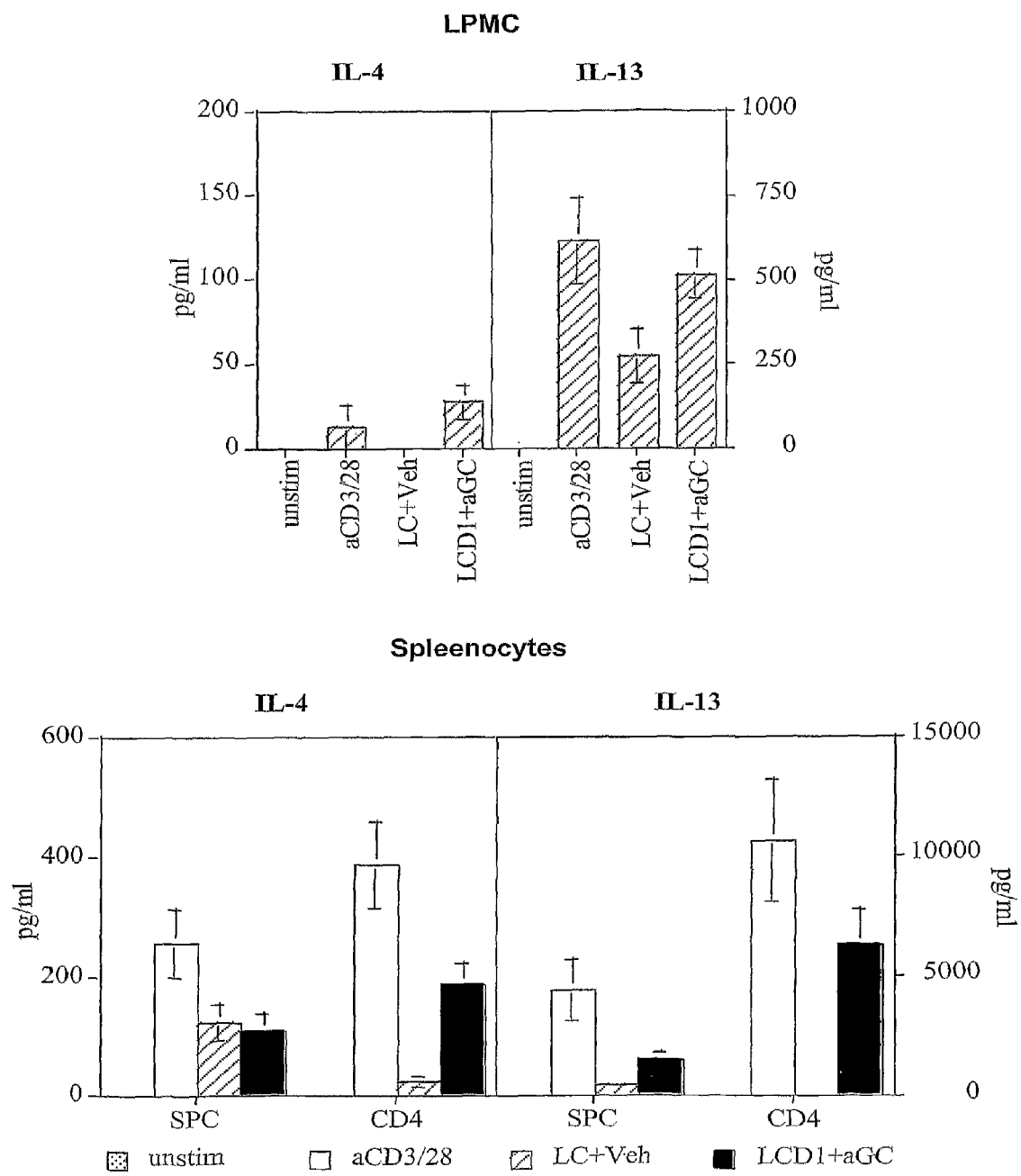
FIG. 6 shows cytokine production in response to αGalCer. LPMC (upper panel), splenocytes or spleen CD4 cells (lower panel) were not stimulated (unstim.) or stimulated with plate-bound anti-CD3 and soluble anti-CD28 (aCD3/28), untransfected L-cells and vehicle (LC+Veh.), or CD1 transfected L-cells and 100 ng/ml αGalCer (LCD1+aGC).

Finally, to investigate the cytokine production of the LPMC and SPC in response to antigen presented by CD1, these cells were stimulated with αGalCer, a synthetic glycolipid that has been found to activate most NK-T cell lines in a CD1-dependent fashion (Kawano et al., 1997). MHC-class II restricted T cells and NK cells are not affected by αGalCer; thus stimulation with αGalCer represents a way to assess NKT cell activation in unseparated cell mixtures. As shown in FIG. 6, when LPMC or SPC from mice with oxazolone colitis were stimulated with αGalCer they produced large amounts of Th2 cytokines, including very high amounts of IL-13. In addition, CD4-positive cells isolated by MACS from LPMC or SPC also responded to αGalCer with very high IL-13 production, indicating that many of the CD4+cells in cell populations from mice with oxazolone colitis are CD1-restricted NK-T cells.

Comparative Studies: Crohn's Disease and Ulcerative Colitis

In studies comparing Crohn's disease patients with ulcerative colitis patients, increased IL-13 production from lamina propia cells of ulcerative colitis patients was observed as compared to Crohn's disease patients. FACS data comparing the two groups also showing an increased number of NK-T cells in the peripheral blood and lamina propria from ulcerative colitis patients as compared to Crohn's disease patients.

Throughout this application, various publications are referenced. The disclosures of these publications in their entireties, as well as the references cited in these publications, are hereby incorporated by reference into this application in order to more fully describe the state of the art to which this invention pertains.

REFERENCES

Balk, S.P., Bleicher, P.A., and Terhorst, C. (1989). Isolation and characterization of a cDNA and gene coding for a fourth CD1 molecule. Proc Natl Acad Sci U S A 86, 252-256.

Bendelac, A. (1995). Positive selection of mouse NK1+ T cells by CD1-expressing cortical thymocytes. J Exp Med 182, 2091-2096.

Bleicher, P.A., Balk, S.P., Hagen, S.J., Blumberg, R.S., Flotte, T.J., and Terhorst, C. (1990). Expression of murine CD1 on gastrointestinal epithelium. Science 250, 679-682.

Blumberg, R.S., Terhorst, C., Bleicher, P., McDermott, F.V., Allan, C.H., Landau, S.B., Trier, J. S., and Balk, S.P. (1991). Expression of a nonpolymorphic MHC class I-like molecule, CD1D, by human intestinal epithelial cells. J Immunol 147, 2518-2524.

Boirivant, M., Fuss, I.J., Chu, A., and Strober, W. (1998). Oxazolone colitis: A murine model of T helper cell type 2 colitis treatable with antibodies to interleukin 4. J Exp Med 188, 1929-1939.

Brown, M.A., and Hural, J. (1997). Functions of IL-4 and control of its expression. Crit Rev Immunol 17, 1-32.

Ceponis, P.J., Botelho, F., Richards, C.D., and McKay, D.M. (2000). Interleukins 4 and 13 increase intestinal epithelial permeability by a phosphatidylinositol 3-kinase pathway. Lack of evidence for STAT 6 involvement. J Biol Chem 275, 29132-29137.

Chen, H., and Paul, W.E. (1997). Cultured NK1.1+ CD4+T cells produce large amounts of IL-4 and IFN- gamma upon activation by anti-CD3 or CD1. J Immunol 159, 2240-2249.

Cui, J., Shin, T., Kawano, T., Sato, H., Kondo, E., Toura, I., Kaneko, Y., Koseki, H., Kanno, M., and Taniguchi, M. (1997). Requirement for Valphal4 NKT cells in IL-12-mediated rejection of tumors. Science 278, 1623-1626.

Donaldson, D.D., Whitters, M.J., Fitz, L.J., Neben, T.Y., Finnerty, H., Henderson, S.L., O'Hara, R.M., Jr., Beier, D.R., Turner, K.J., Wood, C.R., and Collins, M. (1998). The murine IL-13 receptor alpha 2: molecular cloning, characterization, and comparison with murine IL-13 receptor alpha 1. J Immunol 161, 2317-2324.

Fiorentino, D.F., Zlotnik, A., Vieira, P., Mosmann, T.R., Howard, M., Moore, K.W., and O'Garra, A. (1991). IL-10 acts on the antigen-presenting cell to inhibit cytokine production by Th1 cells. J Immunol 146, 3444-3451.

Fort, M.M., Cheung, J., Yen, D., Li, J., Zurawski, S.M., Lo, S., Menon, S., Clifford, T., Hunte, B., Lesley, R., et al. (2001). IL-25 induces IL-4, IL-5, and IL-13 and Th2-associated pathologies in vivo. Immunity 15, 985-995.

Fuss, I.J., Neurath, M., Boirivant, M., Klein, J.S., de la Motte, C., Strong, S.A., Fiocchi, C., and Strober, W. (1996). Disparate CD4+ lamina propria (LP) lymphokine secretion profiles in inflammatory bowel disease. Crohn's disease LP cells manifest increased secretion of IFN-gamma, whereas ulcerative colitis LP cells manifest increased secretion of IL-5. J Immunol 157, 1261-1270.

Gumperz, J.E., Roy, C., Makowska, A., Lum, D., Sugita, M., Podrebarac, T., Koezuka, Y., Porcelli, S.A., Cardell, S., Brenner, M.B., and Behar, S.M. (2000). Murine CD1d-restricted T cell recognition of cellular lipids. Immunity 12, 211-221.

Hayakawa, K., Lin, B.T., and Hardy, R.R. (1992). Murine thymic CD4+ T cell subsets: a subset (Thy0) that secretes diverse cytokines and overexpresses the V beta 8 T cell receptor gene family. J Exp Med 176, 269-274.

Ishikawa, H., Hisaeda, H., Taniguchi, M., Nakayama, T., Sakai, T., Maekawa, Y., Nakano, Y., Zhang, M., Zhang, T., Nishitani, M., et al. (2000). CD4(+) v(alpha)14 NKT cells play a crucial role in an early stage of protective immunity against infection with Leishmania major. Int Immunol 12, 1267-1274.

Kaneko, Y., Harada, M., Kawano, T., Yamashita, M., Shibata, Y., Gejyo, F., Nakayama, T., and Taniguchi, M. (2000). Augmentation of Valphal4 NKT cell-mediated cytotoxicity by interleukin 4 in an autocrine mechanism resulting in the development of concanavalin A-induced hepatitis. J Exp Med 191, 105-114.

Kawano, T., Cui, J., Koezuka, Y., Toura, I., Kaneko, Y., Motoki, K., Ueno, H., Nakagawa, R., Sato, H., Kondo, E., et al. (1997). CD1d-restricted and TCR-mediated activation of valpha14 NKT cells by glycosylceramides. Science 278, 1626-1629.

Koyasu, S. (1994). CD3+CD16+NK1.1+B220+ large granular lymphocytes arise from both alpha-beta TCR+CD4−CD8− and gamma-delta TCR+CD4−CD8− cells. J Exp Med 179, 1957-1972.

Kumar, H., Belperron, A., Barthold, S.W., and Bockenstedt, L.K. (2000). Cutting edge: CD1d deficiency impairs murine host defense against the spirochete, Borrelia burgdorferi. J Immunol 165, 4797-4801.

Lantz, O., and Bendelac, A. (1994). An invariant T cell receptor alpha chain is used by a unique subset of major histocompatibility complex class I-specific CD4+ and CD4−8− T cells in mice and humans. J Exp Med 180, 1097-1106.

Lee, P. T., Benlagha, K., Teyton, L., and Bendelac, A. (2002). Distinct functional lineages of human V(alpha)24 natural killer T cells. J Exp Med 195, 637-641.

Minty, A., Asselin, S., Bensussan, A., Shire, D., Vita, N., Vyakarnam, A., Wijdenes, J., Ferrara, P., and Caput, D. (1997). The related cytokines interleukin-13 and interleukin-4 are distinguished by differential production and differential effects on T lymphocytes. Eur Cytokine Netw 8, 203-213.

Miyamoto, K., Miyake, S., and Yamamura, T. (2001). A synthetic glycolipid prevents autoimmune encephalomyelitis by inducing TH2 bias of natural killer T cells. Nature 413, 531-534.

Mizoguchi, A., Mizoguchi, E., and Bhan, A.K. (1999). The critical role of interleukin 4 but not interferon gamma in the pathogenesis of colitis in T-cell receptor alpha mutant mice. Gastroenterology 116, 320-326.

Moore, K. W., O'Garra, A., de Waal Malefyt, R., Vieira, P., and Mosmann, T.R. (1993). Interleukin-10. Annu Rev Immunol 11, 165-190.

Neurath, M.F., Fuss, I., Kelsall, B.L., Stuber, E., and Strober, W. (1995). Antibodies to interleukin 12 abrogate established experimental colitis in mice. J Exp Med 182, 1281-1290.

Park, S.H., Roark, J.H., and Bendelac, A. (1998). Tissue-specific recognition of mouse CD1 molecules. J Immunol 160, 3128-3134.

Parronchi, P., Romagnani, P., Annunziato, F., Sampognaro, S., Becchio, A., Giannarini, L., Maggi, E., Pupilli, C., Tonelli, F., and Romagnani, S. (1997). Type 1 T-helper cell predominance and interleukin-12 expression in the gut of patients with Crohn's disease. Am J Pathol 150, 823-832.

Roark, J.H., Park, S.H., Jayawardena, J., Kavita, U., Shannon, M., and Bendelac, A. (1998). CD1.1 expression by mouse antigen-presenting cells and marginal zone B cells. J Immunol 160, 3121-3127.

Sartor, R.B. (1995). Current concepts of the etiology and pathogenesis of ulcerative colitis and Crohn's disease. Gastroenterol Clin North Am 24, 475-507.

Saubermann, L.J., Beck, P., De Jong, Y.P., Pitman, R.S., Ryan, M.S., Kim, H.S., Exley, M., Snapper, S., Balk, S.P., Hagen, S.J., et al. (2000). Activation of natural killer T cells by alpha-galactosylceramide in the presence of CD1d provides protection against colitis in mice. Gastroenterology 119, 119-128.

Scheiffele, F., Fuss, I. (2002). Induction of TNBS colitis in mice, Vol 15.19, John Wiley & Sons, Inc.).

Smiley, S.T., Kaplan, M.H., and Grusby, M.J. (1997). Immunoglobulin E production in the absence of interleukin-4-secreting CD1-dependent cells. Science 275, 977-979.

Sonoda, K.H., Exley, M., Snapper, S., Balk, S.P., and Stein-Streilein, J. (1999). CD1-reactive natural killer T cells are required for development of systemic tolerance through an immune-privileged site. J Exp Med 190, 1215-1226.

Spada, F.M., Koezuka, Y., and Porcelli, S.A. (1998). CD1d-restricted recognition of synthetic glycolipid antigens by human natural killer T cells. J Exp Med 188, 1529-1534.

Strober, S., Cheng, L., Zeng, D., Palathumpat, R., Dejbakhsh-Jones, S., Huie, P., and Sibley, R. (1996). Double negative (CD4−CD8− alpha beta+) T cells which promote tolerance induction and regulate autoimmunity. Immunol Rev 149, 217-230.

Takeda, K., Hayakawa, Y., Van Kaer, L., Matsuda, H., Yagita, H., and Okumura, K. (2000). Critical contribution of liver natural killer T cells to a murine model of hepatitis. Proc Natl Acad Sci U S A 97, 5498-5503.

Terabe, M., Matsui, S., Noben-Trauth, N., Chen, H., Watson, C., Donaldson, D.D., Carbone, D.P., Paul, W.E., and Berzofsky, J.A. (2000). NKT cell-mediated repression of tumor immunosurveillance by IL-13 and the IL-4R-STAT6 pathway. Nat Immunol 1, 515-520.

Urban, J.F., Jr., Noben-Trauth, N., Donaldson, D.D., Madden, K.B., Morris, S.C., Collins, M., and Finkelman, F.D. (1998). IL-13, IL-4Ralpha, and Stat6 are required for the expulsion of the gastrointestinal nematode parasite Nippostrongylus brasiliensis. Immunity 8, 255-264.

Vezys, V., Olson, S., and Lefrancois, L. (2000). Expression of intestine-specific antigen reveals novel pathways of CD8 T cell tolerance induction. Immunity 12, 505-514.

Wills-Karp, M., Luyimbazi, J., Xu, X., Schofield, B., Neben, T.Y., Karp, C.L., and Donaldson, D. D.(1998). Interleukin-13: central mediator of allergic asthma. Science 282, 2258-2261.

Yoshimoto, T., and Paul, W.E. (1994). CD4pos, NK1.1pos T cells promptly produce interleukin 4 in response to in vivo challenge with anti-CD3. J Exp Med 179, 1285-1295.

Zurawski, G., and de Vries, J.E. (1994). Interleukin 13, an interleukin 4-like cytokine that acts on monocytes and B cells, but not on T cells. Immunol Today 15, 19-26.

What is claimed is:

1. A method of treating the inflammatory response of ulcerative colitis in a subject comprising administering to the subject an effective amount of an antibody or antigen-binding fragment thereof that binds to CD1.

2. The method of claim 1, wherein the subject is a human.

3. The method of claim 1, wherein the ulcerative colitis is caused by an inflammatory bowel disorder.

4. The method of claim 1, further comprising administration of an antibody that binds to Vα14 Jα281 or Vα14 Jα18.

* * * * *